(12) United States Patent
Levinski et al.

(10) Patent No.: US 8,913,237 B2
(45) Date of Patent: Dec. 16, 2014

(54) DEVICE-LIKE SCATTEROMETRY OVERLAY TARGETS

(71) Applicant: KLA-Tencor Corporation, Milpitas, CA (US)

(72) Inventors: Vladimir Levinski, Nazareth Illit (IL); Daniel Kandel, Aseret (IL); Eran Amit, Pardes Hanna-Karkur (IL)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 13/904,318

(22) Filed: May 29, 2013

(65) Prior Publication Data

US 2013/0342831 A1   Dec. 26, 2013

Related U.S. Application Data

(60) Provisional application No. 61/664,453, filed on Jun. 26, 2012, provisional application No. 61/792,674, filed on Mar. 15, 2013.

(51) Int. Cl.

| | |
|---|---|
| *G01B 11/27* | (2006.01) |
| *H01L 23/544* | (2006.01) |
| *G01N 21/47* | (2006.01) |
| *G03F 7/20* | (2006.01) |
| *G01N 21/956* | (2006.01) |

(52) U.S. Cl.
CPC ............ *G01B 11/272* (2013.01); *H01L 23/544* (2013.01); *G01N 21/47* (2013.01); *G03F 7/70633* (2013.01); *G01N 21/956* (2013.01)
USPC .................. 356/237.1; 356/237.4; 356/237.5; 356/601

(58) Field of Classification Search
CPC . G01B 11/272; H01L 23/544; G03F 7/70633; G01N 21/47; G01N 21/956
USPC .................. 356/237.1–237.5, 601, 625, 401
See application file for complete search history.

(56) References Cited

U.S. PATENT DOCUMENTS

| | | | | |
|---|---|---|---|---|
| 6,927,080 | B1 * | 8/2005 | Nariman et al. | 438/14 |
| 6,934,024 | B2 * | 8/2005 | Zhan et al. | 356/369 |
| 7,608,468 | B1 * | 10/2009 | Ghinovker et al. | 438/16 |
| 2003/0044702 | A1 | 3/2003 | Schulz | |

(Continued)

OTHER PUBLICATIONS

"Int'l Application Serial No. PCT/US2013/047887, Search Report and Written Opinion mailed Oct. 15, 2013", 11 pgs.

*Primary Examiner* — Sang Nguyen
(74) *Attorney, Agent, or Firm* — Kwan & Olynick LLP (57) ABSTRACT

In one embodiment, a semiconductor target for detecting overlay error between two or more successive layers of a substrate or between two or more separately generated patterns on a single layer of a substrate is disclosed. The target comprises at least a plurality of a plurality of first grating structures having a course pitch that is resolvable by an inspection tool and a plurality of second grating structures positioned relative to the first grating structures. The second grating structures have a fine pitch that is smaller than the course pitch, and the first and second grating structures are both formed in two or more successive layers of a substrate or between two or more separately generated patterns on a single layer of a substrate. The first and second gratings have feature dimensions that all comply with a predefined design rules specification.

18 Claims, 7 Drawing Sheets

(56) References Cited

U.S. PATENT DOCUMENTS

2003/0156276 A1 8/2003 Bowes
2007/0081170 A1 4/2007 Sezginer et al.
2007/0279630 A1* 12/2007 Kandel et al. ................. 356/401
2010/0005442 A1 1/2010 Ghinovker et al.
2010/0091284 A1 4/2010 Mieher et al.
2011/0133065 A1* 6/2011 Nakayama et al. ........ 250/252.1
2011/0249244 A1* 10/2011 Leewis et al. .................... 355/27
2012/0120396 A1* 5/2012 Kandel et al. ................. 356/399

* cited by examiner

DEVICE-LIKE SCATTEROMETRY OVERLAY TARGETS

CROSS-REFERENCE TO RELATED APPLICATIONS

This application claims the benefit of the following prior applications: (i) U.S. Provisional Application No. 61/664,453, filed Jun. 26, 2012, titled "Device-Like Scatterometry Targets" by Daniel Kandel et al. and (ii) U.S. Provisional Application No. 61/792,674, filed Mar. 15, 2013, titled "Device-Like Scatterometry Overlay Targets" by Vladimir Levinski et al., which applications are herein incorporated by reference in their entirety for all purposes.

BACKGROUND OF THE INVENTION

The present invention relates generally to overlay measurement techniques, which are used in semiconductor manufacturing processes. More specifically, the present invention relates to techniques for measuring alignment error between different layers or different patterns on the same layer of a semiconductor wafer stack.

An overlay measurement generally specifies how accurately a first patterned layer aligns with respect to a second patterned layer disposed above or below it or how accurately a first pattern aligns with respect to a second pattern disposed on the same layer. The overlay error is typically determined with an overlay target having structures formed on one or more layers of a work piece (e.g., semiconductor wafer). The structures may take the form of gratings, and these gratings may be periodic. If the two layers or patterns are properly formed, then the structure on one layer or pattern tends to be aligned relative to the structure on the other layer or pattern. If the two layers or patterns are not properly formed, then the structure on one layer or pattern tends to be offset or misaligned relative to the structure on the other layer or pattern.

There continues to be a need for improved overlay targets, as well as techniques and apparatus for measuring and determining overlay.

SUMMARY OF THE INVENTION

The following presents a simplified summary of the disclosure in order to provide a basic understanding of certain embodiments of the invention. This summary is not an extensive overview of the disclosure and it does not identify key/critical elements of the invention or delineate the scope of the invention. This summary's sole purpose is to present some concepts disclosed herein in a simplified form as a prelude to the more detailed description that is presented later.

In general, certain embodiments of the present invention comprise a target having gratings that are arranged to facilitate a scatterometry type inspection process. The gratings can be characterized by two scales—a coarse pitch and fine pitch. The fine pitch is a design rule compliant pitch, and the whole grating, including the course and fine gratings, also form a design rule compliant grating, the duty cycle of which changes with periodicity corresponding to the coarse pitch size. This change within one period can be continuous or discrete.

In one embodiment, a semiconductor target for detecting overlay error between two or more successive layers of a substrate or between two or more separately generated patterns on a single layer of a substrate is disclosed. The target comprises at least a plurality of a plurality of first grating structures having a course pitch that is resolvable by an inspection tool and a plurality of second grating structures positioned relative to the first grating structures. The second grating structures have a fine pitch that is smaller than the course pitch, and the first and second grating structures are both formed in two or more successive layers of a substrate or between two or more separately generated patterns on a single layer of a substrate. The first and second gratings have feature dimensions that all comply with a predefined design rules specification.

In a specific implementation, the second grating structures are arranged between each pair of first grating structures so that a plurality of spaces of the first and second grating structures complies with the predefined design rules specification while the course pitch would not comply with the predefined design rules specification without the second grating structures. In another implementation, a duty cycle varies between the first and second grating structures. In another aspect, the first and second grating structures have a plurality of different critical dimension (CD) values. In a further aspect, the first grating structures have a first set of CD values for line width and spacing width and the second grating structures have a second set of CD values for line width and spacing width. The second set of CD values differs from the first set of CD values. In yet a further aspect, the first set of CD values varies across a cycle of the course pitch.

In another embodiment, the first and second grating structures are a plurality of holes formed in two or more successive layers of a substrate or between two or more separately generated patterns on a single layer of a substrate and such holes have a plurality of CD values that vary. In another embodiment, the course pitch is selected to enhance $1^{st}$ order diffraction from the first and second grating, while minimizing other diffraction orders. In a further aspect, the first and second gratings are both formed in a first layer and a second layer, which differs from the first layer, and the first and second set of CD values comprise a subset of CD values that are selected to equalize an amplitude of a signal measured from the first and second gratings in both the first and second layers during a scatterometry inspection process.

In another embodiment, the invention pertains to a method of manufacturing a semiconductor target for detecting overlay error between two or more successive layers of a substrate or between two or more separately generated patterns on a single layer of a substrate. The method includes forming one or more of the above described targets.

In another embodiment, the invention is directed towards an apparatus for detecting overlay error between two or more successive layers of a substrate or between two or more separately generated patterns on a single layer of a substrate. The apparatus comprises at least a scatterometry module for obtaining scatterometry signals from an overlay target having a plurality of first grating structures having a course pitch that is resolvable by the inspection apparatus and a plurality of second grating structures positioned relative to the first grating structures, wherein the second grating structures have a fine pitch that is smaller than the course pitch, wherein the first and second grating structures are both formed in two or more successive layers of a substrate or between two or more separately generated patterns on a single layer of a substrate. The apparatus further comprises a processor configured to analyze the obtained scatterometry signals to thereby determine overlay error within such targets. In a specific implementation, the scatterometry module includes an illumination module oriented to scan radiation across the overlay target, wherein the illumination module comprises an objective lens and a solid immersion lens positioned between the objective lens and the overlay target, and one or more detectors oriented to detect the scatterometry signal which has scattered from the overlay target in response to the radiation scanned across the overlay target. In one aspect, the solid immersion lens is an aplanatic lens with a planar front surface.

These and other features of the present invention will be presented in more detail in the following specification of embodiments of the invention and the accompanying figures which illustrate by way of example the principles of the invention.

BRIEF DESCRIPTION OF THE DRAWINGS

FIG. 6(*a*) is a side view illustration of a patterned top layer L2 being offset by a predefined offset, +f, from a patterned bottom layer L1 in accordance with one embodiment of the present invention.

FIG. 6(*b*) is a side view illustration of a patterned top layer L2 being offset by a predefined offset, +f, and an overlay error, +ϵ, from a patterned bottom layer L1 in accordance with one embodiment of the present invention.

FIG. 6(*c*) is a side view illustration of a patterned top layer L2 being offset by a predefined offset, -f, from a patterned bottom layer L1 in accordance with one embodiment of the present invention.

FIG. 6(*d*) is a side view illustration of a patterned top layer L2 being offset by a predefined offset, -f, and an overlay error, +ϵ, from a patterned bottom layer L1 in accordance with one embodiment of the present invention.

DETAILED DESCRIPTION OF SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Scatterometry overlay (SCOL) targets may include two gratings formed in two different fabrication layers or two separately generated patterns of a same layer. To measure alignment between such gratings, incident light can be scattered from the SCOL gratings and a spectra is measured and obtained from the SCOL grating based on the scattered light. The spectra that is measured from the two gratings can then be used to determine overlay error as further described herein.

Figure 1:
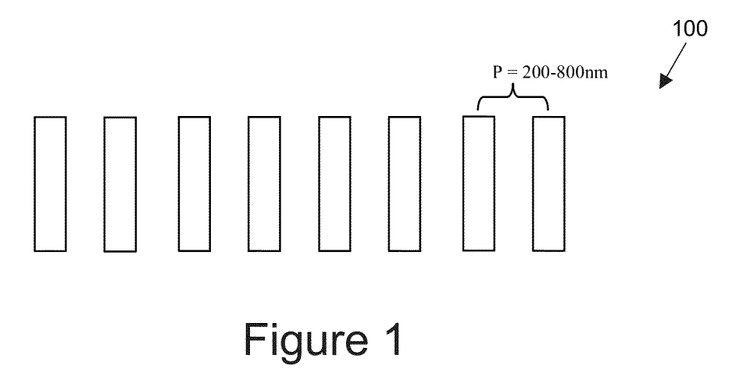
FIG. 1 is a top plan view representation of a grating of a scatterometry overlay (SCOL) target that has dimensions that are noncompliant with design rules.

Current SCOL targets are non-design-rule targets, which can include features or spaces as large as 400 nm. A typical SCOL target has several cells, each of which includes at least two gratings (one in each of the layers to be measured). A top view of a grating 100 in one of these layers is illustrated in FIG. 1. This grating has dimensions that are noncompliant with design rules. For example, the typical size of a feature or a space in this target 100 may be hundreds of nanometers, in contrast, with design rule features, which are tens of nanometers in size.

Figure 2:
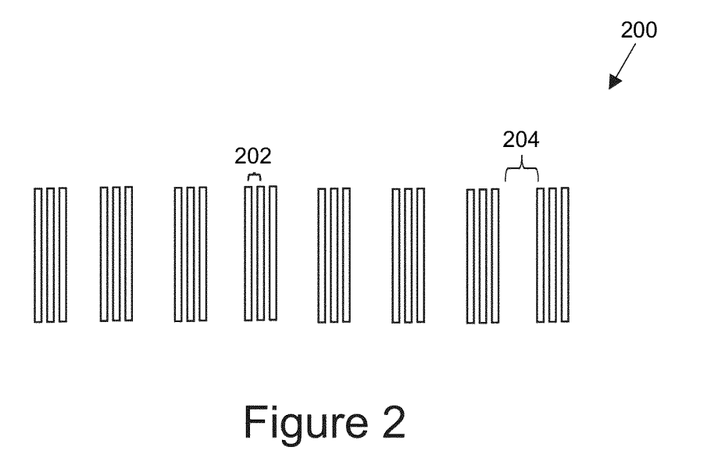
FIG. 2 is a top plan view representation of a grating with fine segments that are compliant with design rules and course segments that are noncompliant with design rules.

The features of a SCOL target may also be segmented for better process compatibility as illustrated in FIG. 2. For example, the SCOL target 200 of FIG. 2 has a fine segmentation pitch 202 that is in the order of tens of nanometers, which is similar to the current design rules for a device. However, the SCOL target 200 also includes spaces 204 in such a segmented target that are not design rule compliant, e.g., having a size of hundreds of nanometers. Therefore, this segmented SCOL target 200 still does not necessarily have the same overlay as a corresponding device, and such overlay may also become distorted and noisy because of process effects.

Figure 3:
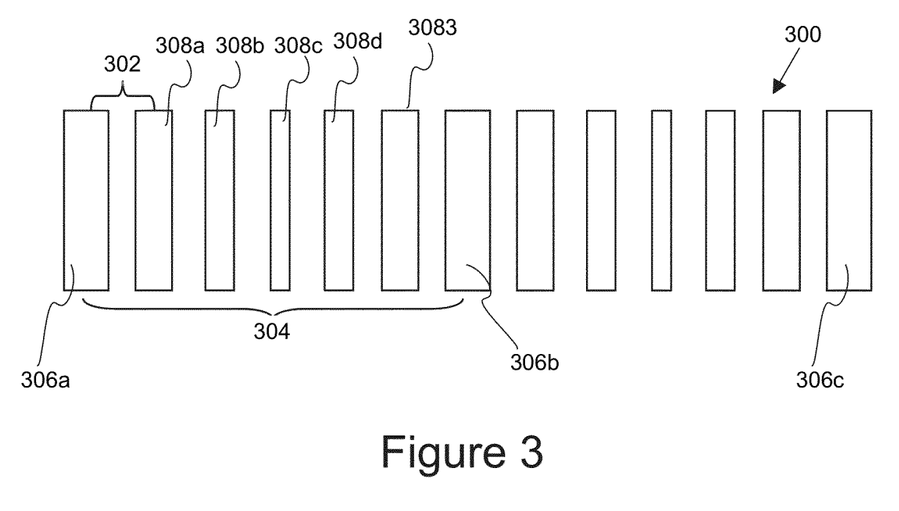
FIG. 3 is a diagrammatic representation of a device-like SCOL target in accordance with a first embodiment of the present invention.

Certain embodiments of the present invention provide targets having gratings with feature dimensions that all meet a predefined set of design rules. FIG. 3 is a diagrammatic representation of a SCOL target 300 in accordance with a first embodiment of the present invention. As shown, the SCOL target includes a course pitch 304 between isolated features (e.g., 306*a*, 306*b*, and 306*c*) having spaces that are each filled with densely packed features that comply with predefined design rules. For instance, dense features 308*a*-308*d* are positioned between isolated features 306*a* and 306*b* so that the course pitch and densely packed feature (with fine pitch) are all design rule compliant.

The duty cycle can vary between (or across) dense and isolated features, as well as for the entire target grating (e.g., the grating has a duty cycle that changes with periodicity corresponding to a coarse pitch size). Since the fine pitch is unresolved by an optical tool, the optical device will see only the coarse pitch which can be larger than 600 nm. It is noted that in this target 300 (in contrast with the targets of FIGS. 1 and 2), all the feature widths and spaces have sizes that are of the order of tens of nanometers and are design-rule compliant.

Figure 4:
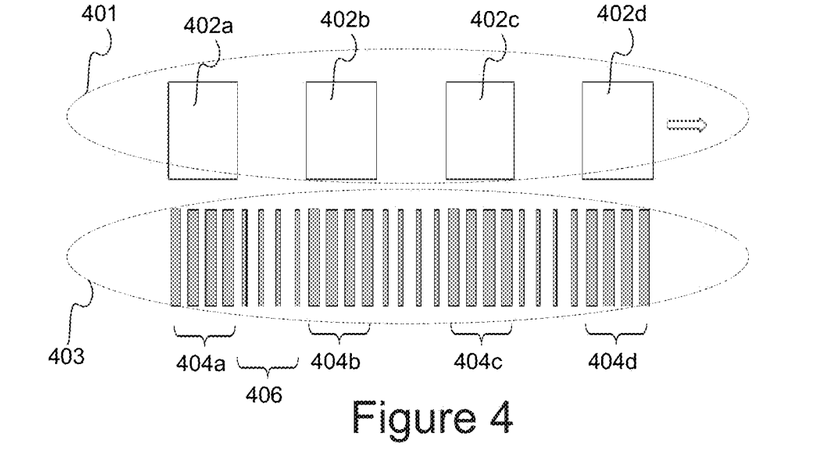
FIG. 4 illustrates a first example of how a standard, large pitch grating can be transformed into a device-like SCOL grating in accordance with one embodiment of the present invention.

FIG. 4 illustrates how a standard, large pitch grating 401 can be transformed into a device-like SCOL grating 403 in accordance with one embodiment of the present invention. In this example, two values of critical dimension (CD) are used, rather than a full distribution of CD's. In this embodiment, isolated grating structures 404a-404d of device-like grating 403 can be formed at positions corresponding to the large pitch structures, e.g., 402a-402d, of grating 401.

As shown, the resulting device-like SCOL target 403 includes isolated structures 404a-404d having a first set of CD values for line width and spacing. The device-like SCOL target 403 also include dense structures, which have a second set of CD values for line width and spacing, between each isolated structure. For example, dense structures are positioned in the space 406 between isolated structures 404a and 404b.

Figure 5:
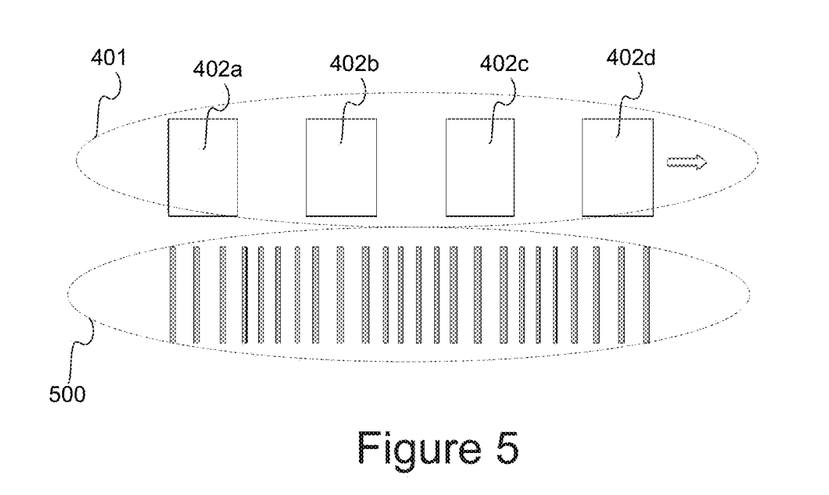
FIG. 5 illustrates a second example of how a standard, large pitch grating can be transformed into a device-like SCOL grating in accordance with another embodiment of the present invention.

The spaces between the lines (or other periodic structures), instead of CD variations, can be used to generate the effective coarse pitch of the device-like SCOL target. Additionally, both the CD and the space dimensions can be varied within a coarse pitch as illustrated in the device-like SCOL grating 500 of FIG. 5.

The same principals can be used to generate any suitable type of design-rule compliant 2D gratings (e.g. holes), with relatively large coarse pitch in either one or two directions. According to one embodiment, structures included in a target may be organized in various configurations and shapes, including, for example, lines, grids, rectangles, squares, curved lines, curved shapes, circles, cylindrical shapes, conical shapes or combinations of the foregoing. Such configurations of structures may be disposed at various locations within the target, and may describe various angles with respect to the electromagnetic radiation incident on the target. For example, the sets of structures could be organized as a set of parallel lines perpendicular to the direction of propagation of a collimated set of radiation rays or of a beam incident on the target. In another case, the structures organized as a set of parallel lines could be disposed at an acute angle with respect to the incident radiation, possibly at an angle of 45 degrees. Such a configuration may facilitate the determination of overlay in both x and y directions, thereby reducing the need for additional overlay patterns or measurements. Alternatively, the incident radiation could be directed to be substantially parallel to at least some of the parallel lines comprising the structures or defining the structures. This technique allows x and y overlay measurements to be performed without rotating the sample.

Additionally, any suitable course pitch overlay target can be transformed into a device-like target. For example, any of the periodic structures described in U.S. Pat. No. 7,068,833 by Ghinovker et al., issued 27 Jun. 2006, may be transformed into device-like gratings by forming dense periodic structures between any of the periodic image resolvable structures of this patent. This patent U.S. Pat. No. 7,068,833 is incorporated herein by reference in its entirety. If the resulting device-like target is expected to result in a low contrast detected signal, a smaller leading frequency bandwidth may be used to compensate for low contrast during the signal measurement In one embodiment, the device-like target may be formed from a plurality of holes having a CD (e.g., hole width) that varies, while keeping the sum of the CD and spacing constant, for example, with a value between 30-150 nm (in general, this value does not have to be constant, only small enough to keep within the design rules). The duty cycle may change with a periodicity of 200-1500 nm, which defines the measurable coarse pitch. The periodicity and the holes CD can be different for x and y.

Figure 9:
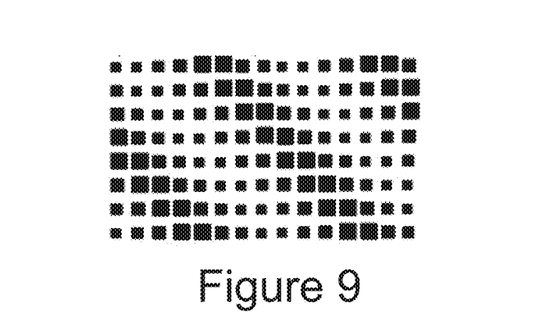
FIG. 9 illustrates a device-like target formed from a plurality of holes having different shapes in accordance with an alternative embodiment of the present invention.

The coarse pitches of the different layers do not have to be identical. For example, one of the layers in a device-line SCOL target may have a coarse pitch of 500 nm, while the other has a coarse pitch of 100 nm (e.g., target periodicity is 500 nm). In addition, the hole shapes do not have to be identical. Rectangular holes, circular holes or lines can be part of the same target. FIG. 9 illustrates a device-like target formed from a plurality of holes having different shapes in accordance with an alternative embodiment of the present invention.

The device-like gratings may be formed in two different layers of a sample, such as a semiconductor wafer, or in two separately generated patterns in a same layer of a sample. Overlay between two layers or two separately generated patterns in the same layer may be determined in any suitable manner. In one SCOL technique, two device-like gratings having a predefined offset with respect to each other are formed in two different layers. The offsets are generally selected so that overlay may be determined from the spectra measured from such target gratings without using calculated theoretical or calibration data. In the following examples, the gratings of each layer are simplified to include gratings structures having a single set of CD parameters so as to simplify the description of overlay determination. However, different grating structures having different CD parameters may be formed in each layer of the target. For instance, other grating structures having different CD line widths may be formed between the illustrated grating structures.

Figure 6A:
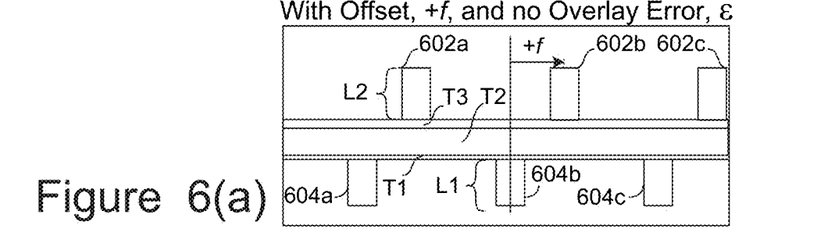

FIG. 6(a) is a side view illustration of a patterned top layer L2 that is offset by a predefined offset, +f, from a patterned bottom layer L1 in accordance with one embodiment of the present invention. Each layer L1 and L2 is patterned into a set of structures. A structure may include any suitable grating feature, such as a line, trench or a row of contacts or other type structures. A structure may be designed to be similar to a semiconductor device feature. A structure may also be formed from a combination of different features. Further, a structure may be located on any layer of the sample, e.g., either above the top layer of the sample, within any layer of the sample, or partially or completely within a layer of the sample. In the illustrated embodiment of FIG. 6(a), layer L1 includes the complete structures 604a-c, while layer L2 includes the complete structures 602a-c.

As shown, the structures of the top layer L2 are offset by an amount +f from the structures of the bottom layer L1. The structures of the two offset layers may be located within adjacent layers or have any suitable number and types of layers disposed in between the two offset layers. FIG. 6(a) also shows three films T1, T2, and T3 between patterned layers L1 and L2 and their corresponding structures. To the extent that any other layers exist between the two layers having the structures, these other layers exhibit at least a minimum degree of transmission for electromagnetic radiation to permit propagation of the radiation between the layers having the structures. If the intervening layers are opaque, these layers would typically have a minimum degree of topography induced by the bottom grating to permit measurement of radiation reflected from that topography.

Figure 6B:
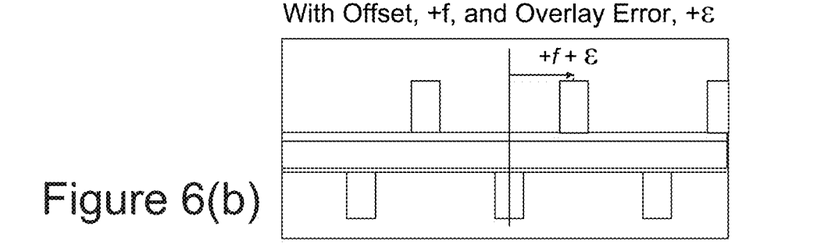
Figure 6C:
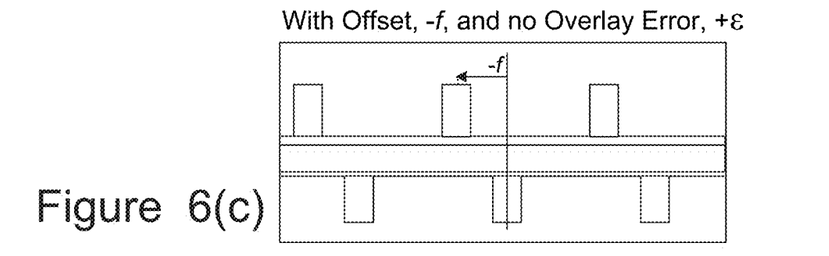
Figure 6D:
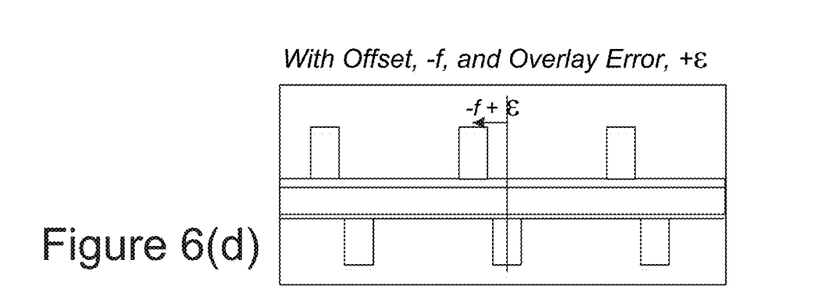

FIG. 6(b) is a side view illustration of a patterned top layer L2 being offset by a predefined offset, +f, and an overlay error, +~, from a patterned bottom layer L1 in accordance with one embodiment of the present invention. FIG. 6(c) is a side view illustration of a patterned top layer L2 being offset by a predefined offset, −f, from a patterned bottom layer L1 in accordance with one embodiment of the present invention. FIG. 6(d) is a side view illustration of a patterned top layer L2 being offset by a predefined offset, −f, and an overlay error, +~, from a patterned bottom layer L1 in accordance with one embodiment of the present invention.

Any suitable technique may be used to determine overlay from the device-like targets described herein. In one embodiment, the device-like targets are comprised of cells. Each cell includes at least a first grating structure formed by a first process and a second grating structure formed by a second process and wherein each cell has a predefined offset between such each cell's first and second grating structures. The first and second grating structures of the different cells may have the same or different predefined offsets. For example, each predefined offset of each cell may be selected to cause one or more terms to be cancelled from a periodic function that represents radiation scattered and measured from each cell. The scattered radiation of each cell may be represented, for example, with a periodic function having a plurality of unknowns parameters, including an unknown overlay error, and the unknown overlay error is determined based on analysis of the plurality of periodic functions for the plurality of cells.

Figure 7:
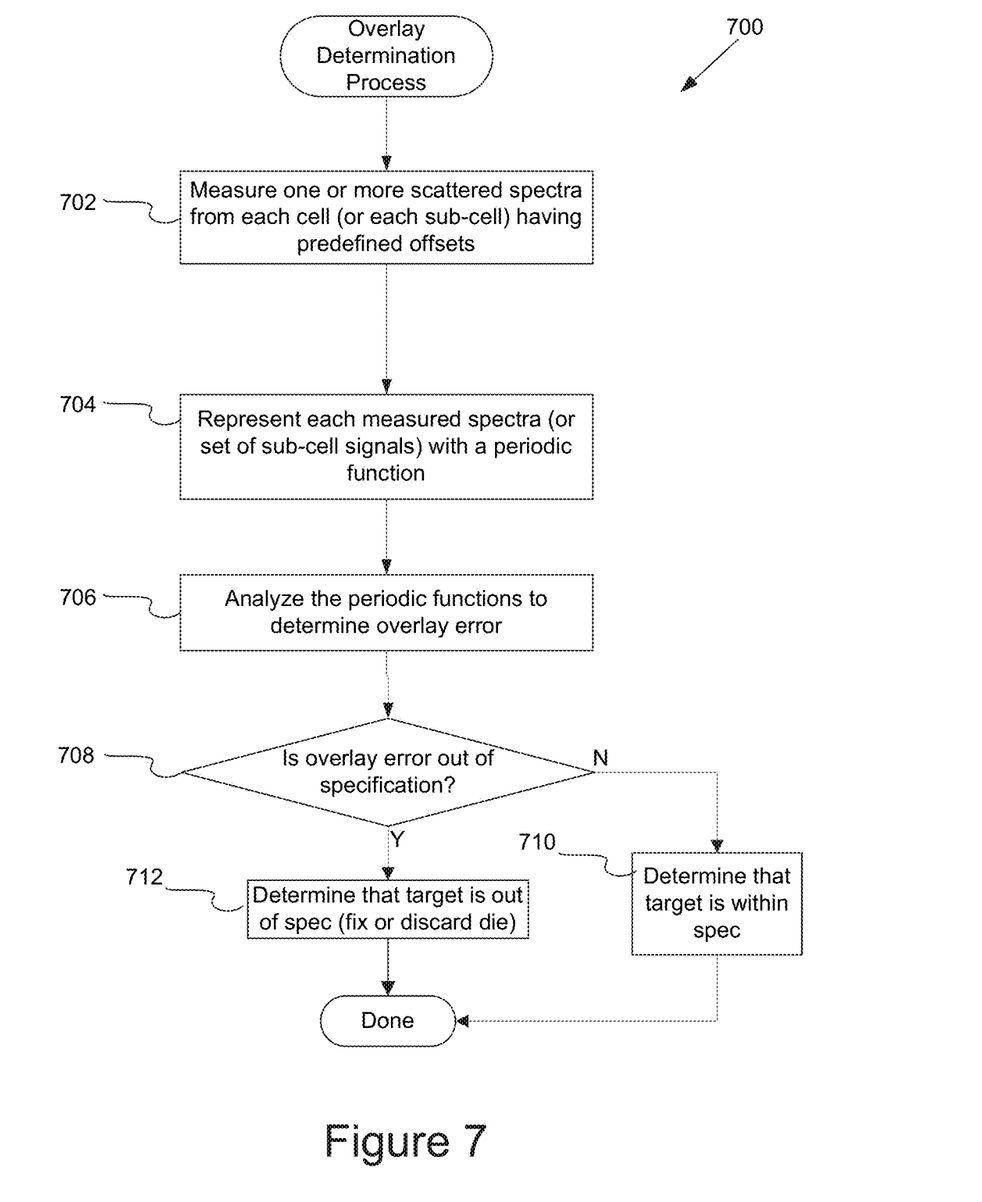
FIG. 7 is a flow chart illustrating a procedure for determining overlay error in accordance with one embodiment of the present invention.

FIG. 7 is a flow chart illustrating a procedure 700 for determining overlay error in accordance with one embodiment of the present invention. Initially, one or more scattered spectra are measured from each cell (or each sub-cell) having predefined offsets in operation 702. For instance, an incident radiation beam is directed towards each of the cell structures (or to each sub-cell structure of each cell) having a predefined offset to measure radiation scattered from such structures. The measurements may be carried out sequentially or simultaneously depending on the measurement system's capabilities. The incident beam may be any suitable form of electromagnetic radiation, such as laser, light emitting diode (LED), or broadband radiation.

Although the scatterometry techniques of the present invention are described as utilizing measured spectra or scattered radiation from a plurality of cells or sub-cells, any suitable type of measurable signal obtained from an overlay target may be used to practice the techniques of the present invention. Example signals include, but are not limited to, any type of spectroscopic ellipsometry or reflectometry signals, including: $\psi$, $\Delta$, Rs (complex reflectivity of the s polarization), Rp (complex reflectivity of the p polarization), Rs ($|r_s|^2$), Rp ($|r_p|^2$), R (unpolarized reflectivity), $\alpha$ (spectroscopic "alpha" signal), $\beta$ (spectroscopic "beta" signal), and functions of these parameters, such as $\tan(\psi)$, $\cos(\Delta)$, ((Rs−Rp)/(Rs+Rp)), etc. The signals could alternatively or additionally be measured as a function of incidence angle, detection angle, polarization, azimuthal angle of incidence, detection azimuthal angle, angular distribution, phase, or wavelength or a combination of more than one of these parameters. The signals could also be a characterization of a combination of signals, such as an average value of a plurality of any of the above described ellipsometry and/or reflectometry signal types. The signals may alternatively take the form of a characteristic of one or more signal(s), such an intensity value(s) or a combination (e.g., average or addition) of intensity values. Other embodiments may use monochromatic or laser light sources where at least one of the signals may be obtained at a single wavelength instead of at multiple wavelengths.

Examples of optical systems and methods for measuring scatterometry signals to determine overlay may be found in U.S. Pat. No. 7,298,481, issued 20 Nov. 2007 by Mieher et al., which patent is herein incorporated by reference in its entirety. Further embodiments of suitable measurement systems and their use for determining overlay error are further described in this 7,298,481 patent.

After measurements are obtained from each target, each measured spectra or signal (or set of sub-cell spectra) can then be represented with a periodic function, such as a Fourier series, in operation 704. In this function, one or more terms may cancel out due, in part, to the predefined offsets.

The representative functions may then be analyzed to determine overlay error c in operation 706. For instance, the plurality of periodic functions each include a plurality of unknowns, including an unknown overlay error, and these periodic functions can be used to determine the unknown overlay error. The measured spectra from the cells (or sub-cells) may be used to determine overlay of structures located at least partially in more than one layer, but could also be used to determine overlay of structures located substantially in a single layer.

It may then be determined whether the measured overlay error is out of specification in operation 708. If the overlay error is not significant (more than the predetermined value), it may be determined that the target is within specification in operation 710. For example, it may be determined that there is no or minimal overlay error between the different layer structures.

If the overlay error is out of specification, it can then be determined that the target is out of specification in operation 712. That is, significant overlay error is present between two or more layer of structures. When a significant overlay error is found, the die can be either discarded or repaired. If a process is out of specification, a number of techniques may be implemented to alleviate the problem. In a first technique, a subsequent process may be adjusted to compensate for the process which is out of specification. In an additional or another technique, the photoresist may then be stripped and reapplied in a corrected pattern to eliminate a misalignment if it is determined that the photoresist pattern is misaligned in any portion.

The targets disclosed herein can be measured by any standard SCOL apparatus. For example, such device-like targets can be measured using a spectroscopic reflectometer or ellipsometer or using an angle-resolved scatterometer with pupil imaging. In one example implementation, a specific diffraction order (typically $0^{th}$ or $1^{st}$ order) may be measured, while other different diffraction orders are not detected and analyzed. In some embodiments, the disclosed targets can be measured with any either $0^{th}$ or $1^{st}$ order, but it would be beneficial to use $1^{st}$ order. Measuring the $0^{th}$ order reflection from these targets cam be very insensitive to overlay. The $1^{st}$ order diffraction can be weak, but its sensitivity to overlay is generally high. An optimal measurement mode could use a very bright light source, such as a laser, to measure only the $+1^{st}$ and $-1^{st}$ orders. It may also be beneficial to block the $0^{th}$ order reflection before it reaches the detector in order to avoid extreme saturation of the detector.

For $1^{st}$ order measurements, the target 300 of FIG. 3, for example, may be used with the dependence of the size of the features within a coarse pitch optimized to enhance $1^{st}$ order diffraction from the grating, while minimizing other diffraction orders. This configuration may enhance the accuracy and precision of the measurement.

For SCOL targets, the control on the diffraction orders that are captured by the collection pupil (determined by the coarse pitch and the illumination wavelength) can enable analysis algorithms that may use higher diffraction orders and also coupling between the different orientations and orders (e.g., $1^{st}$ order in x is coupled with $1^{st}$ order in y). This technique can be used, for example, to design two cells (or even one cell) target with a 2D lattice (such as holes lattice) that differ in the intended overlay in x and y simultaneously. Combined with information obtained by using different measurement conditions (polarization, wavelength and so on) if needed, this small target may provide the same or even more information regarding the overlay error.

A 1st-order scatterometry approach may have an associated precision deterioration due to different diffraction effectiveness of different layers. Usually the amplitude of, for example, $1^{st}$ diffraction order obtained from the upper resist layer is significantly larger than amplitude of the $1^{st}$ diffraction order obtained from the bottom process layer. Further interference of the corresponding diffraction orders in the pupil may also lead to large DC and relatively small amplitude of signal containing OVL information. In order to overcome this problem, a device-like target may be designed to effectively reduce the amplitude of a diffraction order corresponding to the layer (usually upper layer) with larger diffraction effectiveness.

Figure 10A:
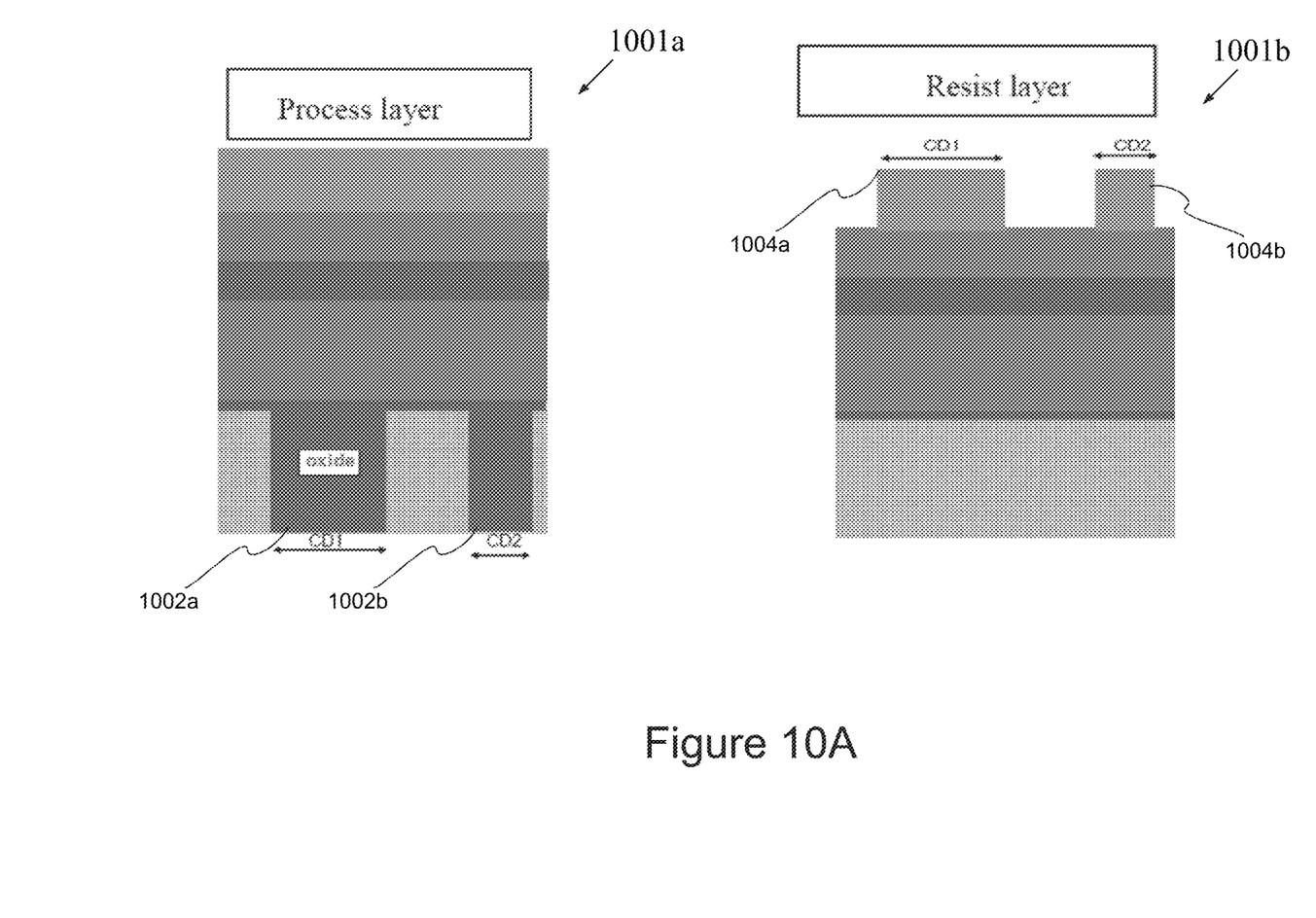
FIG. 10A is a diagrammatic side view of layer stacks having design-like gratings in different layers.

FIG. 10A is a diagrammatic side view of a layer stack 1001*a* containing a lower process layer, such as oxide, with initially designed grating (e.g., 1002*a*) having a pitch P and first critical dimension CD1 and a layer stack 1001*b* containing an upper process layer, such as photoresist, with initially designed grating (e.g., 1004*a*) having a same P and CD1. An additional grating (e.g., 1002*b* and 1004*b*) may be added to each initial design grating, and such additional grating may have the same pitch as the initial grating and a different critical dimension CD2 shifted relative the original grating on half period, by way of example.

Figure 10B:
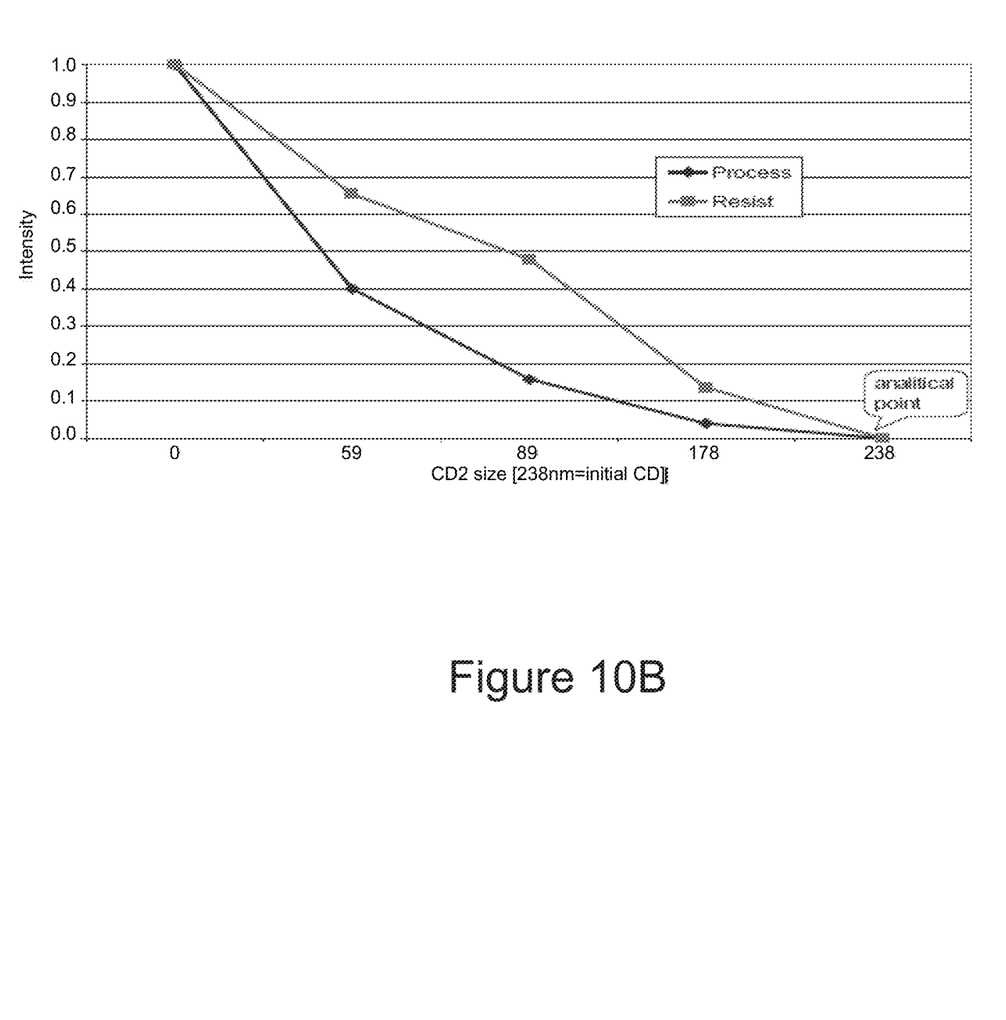
FIG. 10B is a graph illustrating intensity as a function of an additional CD that has been added to device-like target gratings.

FIG. 10B is a graph illustrating intensity as a function of an additional CD grating that has been added to device-like target gratings. As shown, the intensity amplitude of $1^{st}$ diffraction order of the layer grating is set to 1.0 (100%) when CD2=0. Additionally, an amplitude of $1^{st}$ diffraction order of zero corresponds to CD2=CD1. Accordingly, when 0<CD2<CD1, the amplitude of the first order changes monotonically with CD2 change, e.g., R~100%*(CD1−CD2)/CD1. The results of an RCWA (rigorous wave coupled analysis) based simulation of a specific stack taken as an example is shown in FIG. 10B. Thus, a specific CD2 value can be selected to lower the amplitude of the corresponding layer grating (e.g., upper layer) so that the amplitudes from all layer gratings are equalized.

A CD2 grating can also be added to the design-rule like targets. By changing the CD modulation range, which determines amplitudes of diffraction orders corresponding to the coarse pitch, the amplitudes of diffraction orders from both layers can be equalized and substantially improve the precision of overlay measurement.

Certain embodiments of the device-like targets may require less spatial averaging, and a smaller area of the grating may be sufficient for optimal metrology accuracy. Small spot lasers may be used to enable a very small target size (e.g., 2-3 µm).

The spatial coherence of an apparatus with such a small spot is very high, and therefore the measurement can be very sensitive to defects and dust in the optics. Such defects create speckles, which may lead to performance and accuracy penalties. To avoid such penalties, the inspection tool may also include mechanisms for handling spatial coherence. For example, the tool may be configured to perform an angular scan in a pupil plane with a scanning mirror, and average the signal over the scan to calculate the overlay. This scan averages over different areas of optical surfaces and may significantly reduce the effect of optical imperfections and dust. The downside of such a scan is that it can also sample different areas on the target. Accordingly, a larger target may be used.

The inspection tool may also be configured to provide a separate wafer scan (e.g. with the wafer stage), in addition to an optics scan. The wafer scan can be synchronized with the optics scan, so that the illumination spot position movement in the field plane caused by the optical scan in the pupil plane is compensated by the target movement provided by the stage, which effectively cancels the target scan induced by the scan of the optics. The end result is an apparatus which scans over optical surfaces, but is stationary over a single position on the wafer. Solid immersion may also be used for the measurement of the device-like SCOL targets disclosed herein. This apparatus may include, for example, an angle resolved scatterometer with an additional solid immersion lens between the objective lens and the wafer. The solid immersion lens may be an aplanatic lens with a planar front surface. Several embodiments of apparatus and methods, which may be used with the targets of the present invention, are described further in U.S. Provisional Application No. 61/664,477 by Noam Sapiens et al, entitled "Solid Immersion for Semiconductor Metrology, Near-Field Optical Device for Semiconductor Metrology, System and Methods for Reducing Noise in an Angular Resolved Reflectometer, which application is incorporated herein by reference in its entirety.

Several of the techniques of the present invention may be implemented using any suitable combination of software and/or hardware system. For example, the techniques may be implemented within an overlay metrology tool. Preferably, such metrology tool is integrated with a computer system which implements many of the operations of this invention. Such composite system preferably includes at least a scatterometry module for obtaining scatterometry signals of the overlay targets, and a processor configured to analyze the obtained scatterometry signals to thereby determine overlay error within such targets. At a minimum, the scatterometry module will usually include (i) a source of illumination oriented to direct radiation onto a specified location of the sample; and (ii) one or more detectors oriented to detect a scatterometry signal which has been scattered by the sample.

At least a portion of the techniques of the present invention may also be implemented in an overlay metrology system as an additional overlay measurement capability which complements an overlay measurement system or sub-system based on image analysis such as one used for conventional box-in-box or frame-in-frame overlay targets or other imaging type overlay measurement structures.

Regardless of the system's configuration, it may employ one or more memories or memory modules configured to store data, program instructions for the general-purpose inspection operations and/or the inventive techniques described herein. The program instructions may control the operation of an operating system and/or one or more applications. The memory or memories may also be configured to store scatterometry data obtained from the targets and overlay error results and optionally other overlay measurement data.

Because such information and program instructions may be employed to implement the systems/methods described herein, embodiments of the present invention relates to machine readable media that include program instructions, state information, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Figure 8:
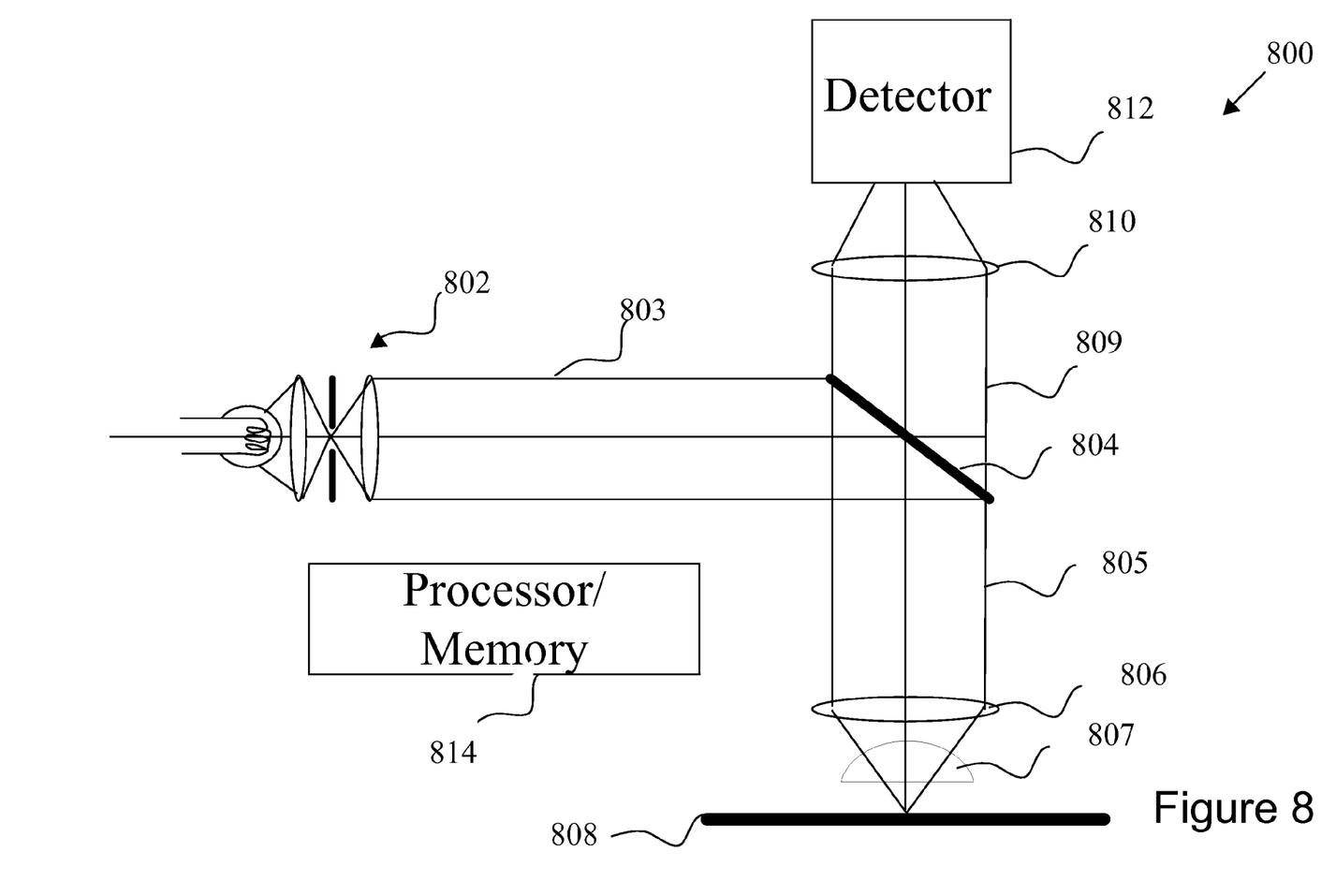
FIG. 8 is a diagrammatic representation of a measurement system in which device-like SCOL targets of the present invention may be measured.

FIG. 8 is a diagrammatic representation of a measurement system 800 in which device-like SCOL targets of the present invention may be measured. As shown, the measurement system 800 includes a beam generator 802 for producing an incident beam 803 of electromagnetic radiation, a beam splitter 804 for directing the incident beam 805 towards the sample 808. Typically, the incident beam is focused onto the sample by a set of illumination lens 806. An output beam 809 is then emitted or scattered from the sample in response to the incident beam and passed through the beam splitter 804 through relay lens 810 onto detector 812. The detector 812 generates a signal of the sample based on the output beam 809.

The system 800 also includes a processor and one or more memory 814 which are configured to control the various components, such as the beam generator 802, illumination lens 806, and detector 812. The processor and memory may also be configured to analyze the detected output beam implementing the various scatterometry techniques described above.

The overlay results obtained with scatterometry overlay techniques described herein may be used to calculate corrections to lithography stepper settings to minimize overlay error. These calculated corrections for lithography steppers or scanners are commonly referred to as "stepper correctables." The stepper correctables obtained from scatterometry overlay measurements may be used as inputs to the stepper to minimize overlay error for subsequent wafer processing. The overlay errors or stepper correctables obtained from scatterometry overlay may be input to an automated process control system which may then calculate a set of stepper corrections to input to the stepper to minimize the overlay errors for subsequent wafer processing. The overlay errors, stepper correctables, or calculated worst overlay errors on the wafer obtained with scatterometry overlay may be used to disposition product wafers to decide if the wafer requires rework or meets overlay requirements for further wafer processing.

The device-like target is designed to follow specific target rules, which preferably include a requirement that the target be placed in a layer which is measurable or inspectable by a particular type of tool. For example, the target may have to be on a top layer or be covered with only optically transparent layers so that the target may be inspected by an optical tool. In other applications, the target may be required to be underneath an opaque layer so that the opaque layer's conformance to the underlying target may be inspected and/or measured. Additionally, each inspection, review, or metrology tool typically has a size constraint as to the measured or inspected structure. That is, structures below a particular size cannot be seen. Therefore, the targets include course pitch structures that are sized so that they can be measured or inspected by the relevant tool.

The device-like targets of the present invention described herein may be placed in any suitable space on the wafer. By way of examples, the targets may be placed in the scribe line or within the dies themselves. When targets are placed in a die, the die layout may also be analyzed to determine whether particular portions or areas have a characteristic which negatively or positively affects metrology or inspection results, as compared with other areas of the die layout. For example, particular layout characteristics may result in more reliable or accurate metrology or inspection results. In one specific case, targets may be placed in areas which have characteristics that positively affect the metrology or inspection. In an example of such a feature characteristic, a chemical mechanical polishing (CMP) procedure is typically tuned to achieve superior accuracy with a particular feature density range. Thus, targets, such as overlay targets, may be placed in layout regions which are within the particular feature density range for an optimal CMP process.

The circuit designer may be aware of feature locations in the die layout which are most susceptible to error or defects. The designer may communicate the position of such features to the target placement software or layout engineer so that targets may be placed proximate to such problem features. This placement technique would likely result in a higher incidence of defect capture and more reliable resulting products.

The targets may also be placed within a dummy layer. It is common practice in semiconductor manufacturing today to include dummy structures in open areas of the circuit layout to ensure uniform pattern density. Dummy structures are generally used for optimal results in chemical mechanical polishing and other semiconductor manufacturing processes.

In order to enable targets inside the chip area, the functionality of the particular metrology (or inspection) target may be combined with the purpose of the dummy structures. That is, a structure which has two components that serve both purposes of a dummy structure and a metrology (or inspection) target would efficiently utilize the open spaces of the die area to increase CMP uniformity (and other dummy requirements where applicable), as well as to provide a metrology or inspection target. Additionally, a new type of metrology or inspection may be used with such combination marks. For example, a particular design pattern's fidelity may be monitored via such combination target. That is, a designer's intent regarding a particular pattern's function or structure may be verified with respect to the pattern being combined and measured or inspected in a dummy structure.

A combination target and dummy structure can be achieved in a number of different ways. An overlay type combination and dummy structure includes two components one on a first layer or mask and one on a second layer or mask. Each component preferably complies with the requirements for a dummy structure of the process step associated with that layer or mask. A further example may be a case where these structures are aligned such that the component on a first mask is symmetrically positioned with respect to the component on a second mask when the masks are correctly aligned. Also, the component on a first mask may be designed to fit into the open spaces within the component on a second mask and vise versa.

When the field of view (FOV) of the inspection tool includes both targets and devices, it may first be determined which parts of the signal are noise (or device structures) and which parts correspond to the target structures. This determination may be accomplished in suitable manner. In one embodiment, the signal (or image generated from such signal) may be compared to a design file which identifies device structures and the device structures' contribution to the signal (or image) is subtracted from the signal (or image). The resulting signal (or image) corresponds to the target which may then be assessed as previously described. Alternatively, one may manually train the metrology tool to locate targets by manually moving the tool to known target locations and identifying the targets. These identified targets can then be used by the metrology tool to search for other targets with a similar appearance using standard pattern recognition techniques. Alternatively, a representative target in the design file may be used to train the metrology tool. The representative target may also be located in a easily found position, such as the scribe line.

In general, rules for both dummy structures and the particular target type are followed when forming combination dummy and target structures. For instance, the dummy structure rules may require a particular pattern density or maximum open space size for ensuring a particular level of CMP uniformity. Additionally, the particular metrology or inspection procedure rules for the targets are followed.

Typically, no significant empty (free of pattern) areas are allowed in modern processes. Unpatterned areas can be filled by dummification structures such that those structures would not introduce any significant cross-talk, when two-dimensional processing is to be used for overlay calculation. One remedy may be to use very deep sub-resolution dummification pitches, so that dummified areas are perceived or measured as "gray" unpatterned ones. Furthermore, tool optics can be designed in a way that dummification pattern is even more suppressed.

The target structures and sub-structures described herein are generally patterned using suitable photolithographic techniques, and the lithographic patterns are subsequently transferred to other materials and layers using established processing techniques such as etching and deposition. In the simplest application, the transferred patterns constitute etched or deposited lines or vias. For example, the structures and sub-structures may be formations of photoresist material, recessed cavity formations, embedded trenches and/or other structures within a wafer layer. The structures and sub-structures formed by cavities may be cavities formed in any of the layers during the semiconductor fabrication process. For example, the cavities may be formed in the photoresist layer, the dielectric material layer, or the metal layers. It should be noted that the above processes are not a limitation and that any suitable fabrication technique may be used.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. A semiconductor target for detecting overlay error between two or more successive layers of a substrate or between two or more separately generated patterns on a single layer of a substrate, the target comprising:
    a plurality of first grating structures having a course pitch that is resolvable by an inspection tool; and
    a plurality of second grating structures positioned relative to the first grating structures, wherein the second grating structures have a fine pitch that is smaller than the course pitch, wherein the first and second grating structures are both formed in two or more successive layers of a substrate or between two or more separately generated patterns on a single layer of a substrate,
    wherein a duty cycle of the first and second gratings changes with periodicity corresponding to a size of the course pitch.

2. The target of claim 1, wherein the second grating structures are arranged between each pair of first grating structures so that a plurality of spaces of the first and second grating structures complies with a predefined design rules specification while the course pitch would not comply with the predefined design rules specification without the second grating structures.

3. The target of claim 1, wherein the first and second grating structures have a plurality of different critical dimension (CD) values.

4. The target of claim 3, wherein the first grating structures have a first set of CD values for line width and spacing width and the second grating structures have a second set of CD values for line width and spacing width that differs from the first set of CD values.

5. The target of claim 4, wherein the first set of CD values vary across a cycle of the course pitch.

6. A semiconductor target for detecting overlay error between two or more successive layers of a substrate or between two or more separately generated patterns on a single layer of a substrate, the target comprising:
    a plurality of first grating structures having a course pitch that is resolvable by an inspection tool; and
    a plurality of second grating structures positioned relative to the first grating structures, wherein the second grating structures have a fine pitch that is smaller than the course pitch, wherein the first and second grating structures are both formed in two or more successive layers of a substrate or between two or more separately generated patterns on a single layer of a substrate,
    wherein the first and second grating structures are a plurality of holes formed in two or more successive layers of a substrate or between two or more separately generated patterns on a single layer of a substrate and such holes have a plurality of CD values that vary.

7. A semiconductor target for detecting overlay error between two or more successive layers of a substrate or between two or more separately generated patterns on a single layer of a substrate, the target comprising:
    a plurality of first grating structures having a course pitch that is resolvable by an inspection tool; and
    a plurality of second grating structures positioned relative to the first grating structures, wherein the second grating structures have a fine pitch that is smaller than the course pitch, wherein the first and second grating structures are both formed in two or more successive layers of a substrate or between two or more separately generated patterns on a single layer of a substrate,
    wherein the course pitch is selected to enhance $1^{st}$ order diffraction from the first and second grating, while minimizing other diffraction orders,
    wherein the first and second gratings are both formed in a first layer and a second layer, which differs from the first layer, and wherein the first and second set of CD values comprise a subset of CD values that are selected to equalize an amplitude of signals measured from the first and second gratings in both the first and second layers during a scatterometry inspection process.

8. An inspection apparatus for inspecting a semiconductor overlay target, comprising:
    at least a scatterometry module for obtaining scatterometry signals from an overlay target having a plurality of first grating structures having a course pitch that is resolvable by the inspection apparatus and a plurality of second grating structures positioned relative to the first grating structures, wherein the second grating structures have a fine pitch that is smaller than the course pitch, wherein the first and second grating structures are both formed in two or more successive layers of a substrate or between two or more separately generated patterns on a single layer of a substrate and wherein a duty cycle of the first and second gratings changes with periodicity corresponding to a size of the course pitch; and
    a processor configured to analyze the obtained scatterometry signals to thereby determine overlay error within such targets.

9. The apparatus of claim 8, wherein the scatterometry modules comprises:
   an illumination module oriented to scan radiation across the overlay target, wherein the illumination module comprises an objective lens and a solid immersion lens positioned between the objective lens and the overlay target; and
   one or more detectors oriented to detect the scatterometry signal which has scattered from the overlay target in response to the radiation scanned across the overlay target.

10. The apparatus of claim 9, wherein the solid immersion lens is an aplanatic lens with a planar front surface.

11. A method of manufacturing a semiconductor target for detecting overlay error between two or more successive layers of a substrate or between two or more separately generated patterns on a single layer of a substrate, comprising:
   forming a plurality of first grating structures having a course pitch that is resolvable by an inspection tool; and
   forming a plurality of second grating structures positioned relative to the first grating structures, wherein the second grating structures have a fine pitch that is smaller than the course pitch, wherein the first and second grating structures are both formed in two or more successive layers of a substrate or between two or more separately generated patterns on a single layer of a substrate,
   wherein a duty cycle of the first and second gratings changes with periodicity corresponding to a size of the course pitch.

12. The method of claim 11, wherein the second grating structures are arranged between each pair of first grating structures so that a plurality of spaces of the first and second grating structures complies with a predefined design rules specification while the course pitch would not comply with the predefined design rules specification without the second grating structures.

13. The method of claim 11, wherein the first and second grating structures have a plurality of different critical dimension (CD) values.

14. The method of claim 13, wherein the first grating structures have a first set of CD values for line width and spacing width and the second grating structures have a second set of CD values for line width and spacing width that differs from the first set of CD values.

15. The method of claim 13, wherein the first set of CD values vary across a cycle of the course pitch.

16. A method of manufacturing a semiconductor target for detecting overlay error between two or more successive layers of a substrate or between two or more separately generated patterns on a single layer of a substrate, comprising:
   forming a plurality of first grating structures having a course pitch that is resolvable by an inspection tool; and
   forming a plurality of second grating structures positioned relative to the first grating structures, wherein the second grating structures have a fine pitch that is smaller than the course pitch, wherein the first and second grating structures are both formed in two or more successive layers of a substrate or between two or more separately generated patterns on a single layer of a substrate,
   wherein the first and second grating structures are a plurality of holes formed in two or more successive layers of a substrate or between two or more separately generated patterns on a single layer of a substrate and such holes have a plurality of CD values that vary.

17. The method of claim 11, wherein the course pitch is selected to enhance $1^{st}$ order diffraction from the first and second grating, while minimizing other diffraction orders.

18. A method of manufacturing a semiconductor target for detecting overlay error between two or more successive layers of a substrate or between two or more separately generated patterns on a single layer of a substrate, comprising:
   forming a plurality of first grating structures having a course pitch that is resolvable by an inspection tool; and
   forming a plurality of second grating structures positioned relative to the first grating structures, wherein the second grating structures have a fine pitch that is smaller than the course pitch, wherein the first and second grating structures are both formed in two or more successive layers of a substrate or between two or more separately generated patterns on a single layer of a substrate,
   wherein the first and second gratings are both formed in a first layer and a second layer, which differs from the first layer, and wherein the first and second set of CD values comprise a subset of CD values that are selected to equalize an amplitude of signals measured from the first and second gratings in both the first and second layers during a scatterometry inspection process.

* * * * *